US00PP28239P2

(12) United States Plant Patent
Park

(10) Patent No.: US PP28,239 P2
(45) Date of Patent: Aug. 1, 2017

(54) ***DIANTHUS* PLANT NAMED 'URIBEST52'**

(50) Latin Name: *Dianthus gratianopolitanus*
Varietal Denomination: Uribest52

(71) Applicant: Uriseed Institute, Icheon-si (KR)

(72) Inventor: Kong Young Park, Icheon-si (KR)

(73) Assignee: URISEED INSTITUTE, Icheon-si (KR)

( * ) Notice: Subject to any disclaimer, the term of this patent is extended or adjusted under 35 U.S.C. 154(b) by 16 days.

(21) Appl. No.: 14/756,898

(22) Filed: Oct. 27, 2015

(51) Int. Cl.
*A01H 5/02* (2006.01)

(52) U.S. Cl.
USPC ..... Plt./282

(58) Field of Classification Search
USPC ..... Plt./282, 277
CPC ..... A01H 5/0233
See application file for complete search history.

*Primary Examiner* — Kent L Bell
(74) *Attorney, Agent, or Firm* — Penny J. Aguirre

(57) ABSTRACT

A new cultivar of *Dianthus* plant named, 'Uribest52', that is characterized by its flowers that are deep red-purple in color, its flowers that are fragrant, its floriferous blooming habit, and its strong stems.

2 Drawing Sheets

Botanical classification: *Dianthus gratianopolitanus.*
Variety denomination: 'Uribest52'.

BACKGROUND OF THE INVENTION

The present invention relates to a new and distinct cultivar of an interspecific hybrid *Dianthus* plant, known as *Dianthus* 'Uribest52' and will be referred to hereinafter by its cultivar name, 'Uribest52'. The new cultivar represents a new herbaceous perennial grown for landscape use.

The new cultivar arose from an ongoing breeding program in Icheon-si, Gyeonggi-do, Korea. The Inventor made cross in 2003 between an unnamed and unpatented plant of *Dianthus alpinus* as the female parent and an unnamed and unpatented plant of *Dianthus callizones* as the male parent. The new cultivar was selected as a single unique plant from the above cross in 2005.

Asexual propagation of the new cultivar was first accomplished using stem cuttings in July 2005 in Icheon-si, Gyeonggi-do, Korea. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Uribest52' as a unique and distinct cultivar of *Dianthus.*

1. 'Uribest52' exhibits flowers that are deep red-purple in color.
2. 'Uribest52' exhibits flowers that are fragrant.
3. 'Uribest52' exhibits a floriferous blooming habit.
4. 'Uribest52' exhibits strong stems.

The parent plants of 'Uribest52' both differ from 'Uribest52' in being shorter in height, in having weak stems and in having very few flowers. 'Uribest52' can be most closely compared to the cultivar 'Neon Star' (U.S. Plant Pat. No. 14,549). 'Neon Star' differs from 'Uribest52' in having flowers that lack fragrance and petals with deeper notches on the apex and that are pinker red in color, and in having longer leaves.

BRIEF DESCRIPTION OF THE DRAWINGS

The accompanying colored photographs illustrate the overall appearance and distinct characteristics of the new *Dianthus*. The photographs in the figures were taken of a plant about 9 months in age as grown in a greenhouse in a 17-cm container in Boskoop, The Netherlands.

The photograph in FIG. 1 provides a side view of a plant of 'Uribest52' in bloom.

Figure 1:
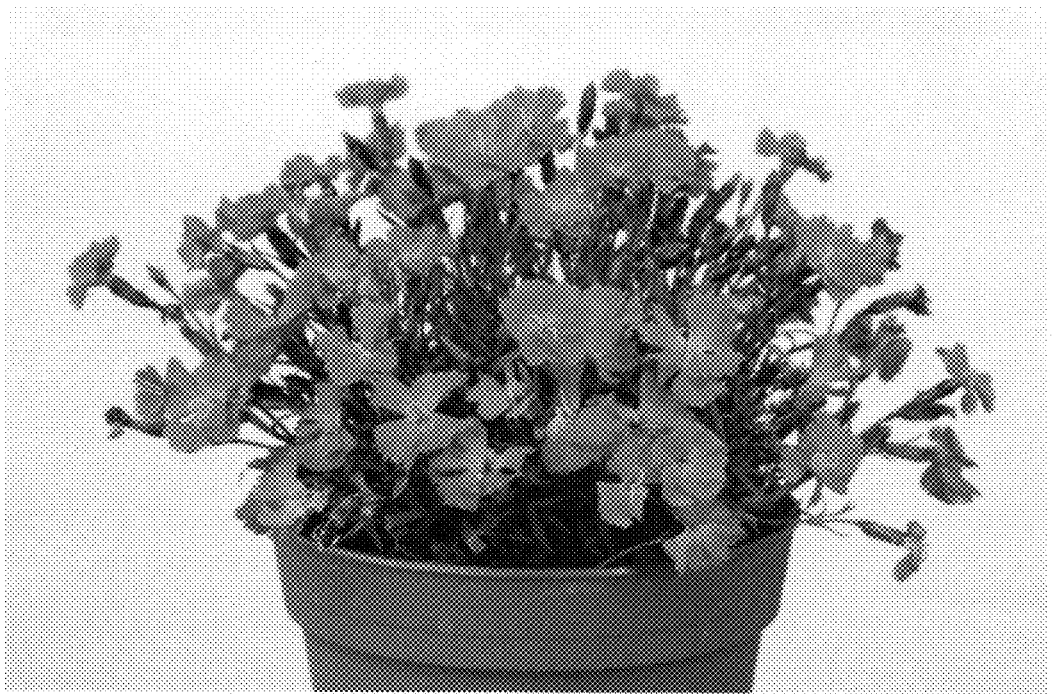
Figure 2:
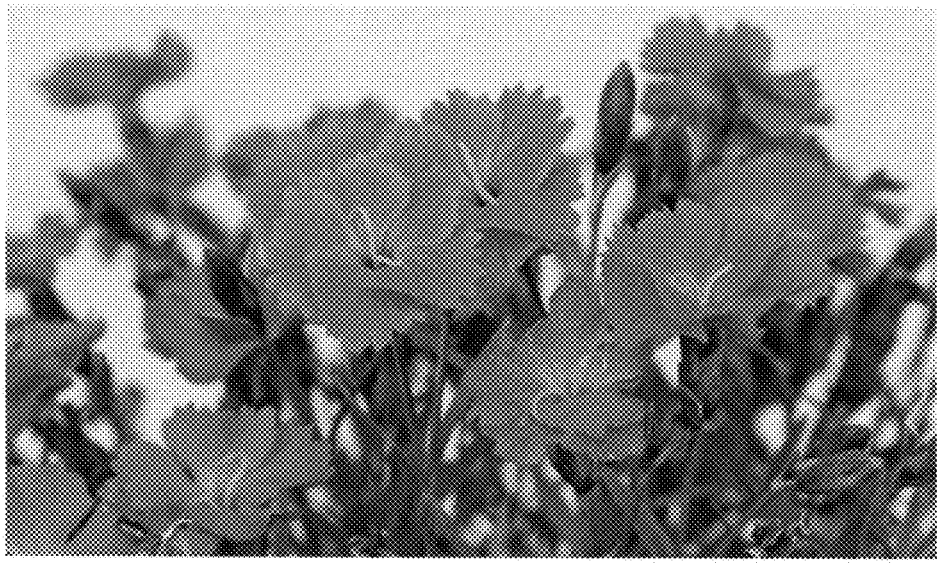

The photograph in FIG. 2 provides a close-up view of the flowers of 'Uribest52'.

Figure 3:
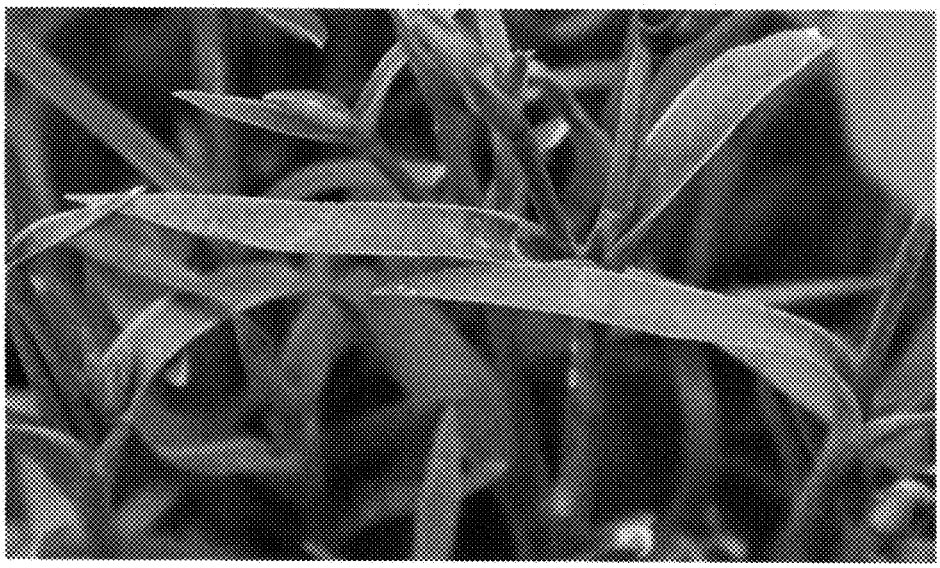

The photograph in FIG. 3 provides a close-up of the foliage of 'Uribest52'.

The colors in the photographs are as close as possible with the digital photography and printing techniques utilized and the color codes in the detailed botanical description accurately describe the colors of the new *Dianthus.*

DETAILED BOTANICAL DESCRIPTION

The following is a detailed description of a plant about 9 months in age as grown as grown in a greenhouse in a 17-cm container in Eoskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms continuously from late spring until late summer in The Netherlands.

*Plant type.*—Herbaceous perennial.

*Plant habit*.—Broadly spreading to upright flattened globular mound of foliage with upright to outward flower scapes.

*Height and spread*.—An average of 15.1 cm in height and 28.2 cm in width.

*Hardiness*.—At least to U.S.D.A. Zone 7.

*Diseases and pests*.—Similar susceptibility and resistance to diseases and pests as other cultivars of *Dianthus* has been observed.

*Root description*.—Fibrous and fine.

*Propagation*.—Stem cuttings.

*Root initiation*.—About 2 to 3 weeks.

*Root development*.—An average of 25 weeks to finish a 9-cm container from a rooted cutting.

*Growth rate*.—Moderate.

Stem description:

*Stem strength*.—Strong.

*Stem aspect*.—Lateral stems held at an average angle of 20° to the main stem.

*Shape*.—Rounded.

*Stem color*.—N138B covered with a thin waxy layer 191C, older stems; 199A.

*Stem size*.—Basal stems; an average of 12 cm in height (excluding peduncle), lateral stems; an average of 6.7 cm in length (excluding peduncle) and 2 mm in diameter.

*Stem surface*.—Glaucous, glabrous, and slightly glossy.

*Branching habit*.—An average of 36 basal stems and 3 lateral stems emerge from the base.

Foliage description:

*Leaf division*.—Simple.

*Leaf shape*.—Narrow oblanceolate to linear.

*Leaf base*.—Decurrent.

*Leaf apex*.—Acute.

*Leaf margin*.—Entire.

*Leaf venation*.—Parallel, not conspicuous, color; upper surface same as leaf color and lower surface main vein; 144A.

*Leaf attachment*.—Sessile, clasping.

*Leaf arrangement*.—Opposite.

*Leaf surface*.—Glabrous and dull on both surfaces.

*Leaf number*.—An average of 14 (7 pairs) per lateral branch.

*Leaf color*.—Newly emerged upper surface; 143A and lower surface; 137D, mature upper surface; a blend between N137C and 189A and lower surface; 137C.

*Leaf size*.—An average of 3.4 cm in length and 4 mm in width.

*Foliage fragrance*.—None.

Flower description:

*Inflorescence type*.—Terminal solitary flowers and occasionally in pairs.

*Lastingness of inflorescence*.—About 10 days, persistent.

*Fragrance*.—Faint and pleasant scent.

*Quantity of flowers*.—About 1 flower per lateral stem.

*Flower type*.—Rotate and solitary.

*Flower size*.—An average of 3 cm in diameter and 2.8 cm in depth.

*Flower buds*.—An average of 1.6 cm in length and 5 mm in width, narrow obovate to oblong in shape, color; 183B to 183C suffused with N186C at the apex.

*Peduncle*.—An average of 1.6 cm in length and 1.25 mm in diameter, 143A in color, smooth surface, held straight on top of flower stem, strong in strength.

*Pedicel*.—Flowers are sessile to peduncle.

*Petals*.—5, rotate, spathulate in shape, margins entire on sides margin with apex praemorse, erose, and crinkled at apex, cuneate base, glabrous, velvety, and dull surface, an average of 3 cm in length and 1.9 cm in width, color; upper surface when opening 61B with base 145B and lower surface 59D with base 145B, upper surface when fully open 61B with base 145B to 145C and lower surface a blend between 59D and 63B with base 145B to 145C, color fades to 63A with base 145B to 145C.

*Calyx*.—Campanulate in shape, an average of 1.4 cm in length and 5 mm in diameter.

*Sepals*.—5, rotate, oblong in shape, entire margin, acute apex, fused base (lower 70% fused into a campanulate shape), an average of 1.4 cm in length and 3 mm in width, dull and glabrous surface, color; immature upper surface 146D and lower surface 183B to 183C and strongly suffused with N186C at the apex, mature upper surface 146D and lower surface 143A suffused with 183C at the apex.

Reproductive organs:

*Gynoecium*.—2 pistils; an average of 2.2 cm in length, extended beyond petals, style; color; 77B to 77D with NN15D at the base, an average of 0.5 cm in length, stigma; feathery, pointed, and curved in shape, 77B in color, ovary; 143C in color.

*Androecium*.—Stamens; 10, filament; NN155A in color, an average of 1.6 cm in length, anthers; 199D in color, narrowly oblong in shape, an average of 1.5 mm in length, pollen; not detected.

*Fruit and seed*.—Not observed.

It is claimed:

1. A new and distinct cultivar of *Dianthus* plant named 'Uribest52' as herein illustrated and described.

* * * * *